United States Patent [19]

Shutt et al.

[11] Patent Number: 4,981,829

[45] Date of Patent: Jan. 1, 1991

[54] OXIDATIVE CONVERSION OF METHANE TO ETHYLENE AND ETHANE

[75] Inventors: Eric Shutt, Benson, United Kingdom; Andries G. Altena, Hengelo Ov., Netherlands; John W. Jenkins, Near Reading, United Kingdom

[73] Assignee: Johnson Matthey Public Limited Company, London, England

[21] Appl. No.: 366,654

[22] Filed: Jun. 15, 1989

Related U.S. Application Data

[62] Division of Ser. No. 84,809, Aug. 13, 1987, Pat. No. 4,873,388.

[30] Foreign Application Priority Data

Aug. 13, 1986 [GB] United Kingdom ................. 8619717

[51] Int. Cl.$^5$ .................................................. B01J 21/02
[52] U.S. Cl. ..................................... 502/202; 502/208; 502/214; 502/232; 502/300; 502/302; 502/303; 502/340; 502/349; 585/500; 585/654; 585/656; 585/700
[58] Field of Search ............... 585/500, 654, 656, 661, 585/700; 502/202, 208, 214, 232, 240, 250, 251, 263, 300, 302, 303, 340, 349

[56] References Cited

U.S. PATENT DOCUMENTS

| 4,495,374 | 1/1985 | Jones | 585/500 |
|---|---|---|---|
| 4,523,049 | 6/1985 | Jones | 585/417 X |
| 4,544,784 | 10/1985 | Sofranko et al. | 585/500 |
| 4,544,785 | 10/1985 | Withers | 585/500 |
| 4,547,607 | 10/1985 | Jones et al. | 585/500 |
| 4,654,460 | 3/1987 | Kimble | 585/500 |
| 4,658,076 | 4/1987 | Kolts | 585/500 |
| 4,665,260 | 5/1987 | Jones | 585/500 |
| 4,670,619 | 6/1987 | Withers et al. | 585/500 |
| 4,826,796 | 5/1989 | Erekson | 502/202 |

FOREIGN PATENT DOCUMENTS 6901645  8/1970  Netherlands ................ 502/202

*Primary Examiner*—Olik Chaudhuri
*Assistant Examiner*—James M. Hunter, Jr.
*Attorney, Agent, or Firm*—Cushman, Darby & Cushman

[57] ABSTRACT

This invention relates to a method for the oxidative conversion of methane to ethylene and/or ethane and to a catalyst system for use in the method.

In more detail a method for the oxidative conversion of methane to ethylene and/or ethane in which a mixture comprising methane and oxygen is heated to a temperature of from 500° to 1000° C. and the heated mixture is contacted with a catalyst system which comprises a first component which is a non-reducible metal compound and which first component is sufficiently refractory to withstand the operative temperature and a second component which is one or more oxycompounds of boron or phosphorus provided on the surface of the first component.

5 Claims, No Drawings

OXIDATIVE CONVERSION OF METHANE TO ETHYLENE AND ETHANE

This is a division of application No. 07/084,809, filed Aug. 13, 1987, now U.S. Pat. No. 4,873,388.

BACKGROUND OF THE INVENTION

This invention relates to a method for the oxidative conversion of methane to ethylene and/or ethane and to a catalyst system for use in the method.

BACKGROUND INFORMATION

Methane is obtained in large quantities from gas and oil fields and as a byproduct of many petrochemical processes, but it has only a few outlets as a chemical raw material and so its main use is as a fuel. Despite seemingly high fuel prices, methane is a commodity of relatively low value and it is not commercially acceptable to incur high costs in its transport. The very low critical temperature of methane (i.e. $-82°$ C.) means that its transport in a liquefied state has become expensive so that nowadays methane fuel is usually transported as a gas by pipeline. If a gas field is too remote from fuel consumers to justify the cost of a pipeline, then the field would not be developed. Alternatively if the field is an oil field, any methane obtained from the oil field would either be flared as waste gas or pumped back underground.

Conversion of methane to ethylene is a well established commercial objective because ethylene has a high value as a chemical raw material. The conversion of methane to ethane is also useful because ethane is easily cracked to make ethylene. The difficulty is that methane is not easily converted to ethylene or ethane. Pyrolysis of methane creates acetylene and/or coke and oxidation of methane usually proceeds uncontrollably to carbon monoxide or carbon dioxide. Attempts at partial oxidation of methane using oxygen supplied by oxidising catalysts have resulted in some conversion to ethylene.

Oxidising catalysts have been based on reducible metal oxides, principally those of Mn, Sn, In, Ge, Sb, Pb. Such catalysts and their use are described, for example, in U.S. patent specifications Nos.: 4,499,322; 4,499,323; 4,517,398; 4,523,049; 4,523,050; 4,544,784; 4,544,785; 4,544,786; 4,544,787; 4,547,607; 4,547,608; 4,547,610; 4,554,395; 4,556,749; 4,560,821; 4,568,785; 4,568,789; 4,629,718; 4,634,800. By "reducible" is meant reducible by methane under the conditions of the reaction and, in most cases, the catalyst was used in a cyclic redox manner, i.e. subjected consecutively to methane and then oxygen-containing gas, the metal oxide being successively reduced and regenerated.

We have now found that oxidative conversion of methane to ethylene and/or ethane can take place on a catalyst system comprising a refractory support which is non-reducible by methane and which carries on its surface a boron or phosphorus moiety.

SUMMARY OF THE INVENTION

Accordingly this invention provides a method for the oxidative conversion of methane to ethylene and/or ethane in which a mixture comprising methane and oxygen is heated to a temperature of from 500° to 1000° C. and the heated mixture is contacted with a catalyst system which comprises a first component which is a non-reducible metal compound and which first component is sufficiently refractory to withstand the operative temperature and a second component which is one or more oxycompounds of boron or phosphorus provided on the surface of the first component.

It has been discovered that the oxycompounds inhibit the total oxidation of methane to carbon monoxide or carbon dioxide and so enable higher yields of ethylene and ethane to be achieved. It is possible that the inhibition arises because the oxycompounds impair the reactivity of the oxygen in the region of the surface of the first component by forming transient compounds of a nature which is not yet fully understood.

Preferably the mixture of methane and oxygen is heated to a temperature of at least 750° C.

DETAILED DESCRIPTION OF THE INVENTION

The metal compound is one of invariant cation oxidative state. Suitable compounds include: BeO, MgO, CaO, SrO, BaO $Sc_2O_3$, $Y_2O_3$, $La_2O_3$ $ZrO_2$, $HfO_2$, $Ta_2O_5$ ZnO, $GeO_2$, $SiO_2$, SiC, BN $Nd_2O_3$, $Gd_2O_3$, $Dy_2O_3$, $Ho_2O_3$, $Er_2O_3$, $Lu_2O_3$ Preferred compounds are ZnO, CaO, $SiO_2$, SiC, BN B and Si, though borderline cases, may be regarded as metals. The above compounds are to be compared in the Examples with compounds which are of multivalent cation oxidative state such as chromium oxide and titanium oxide.

The first component may be doped with one or more moieties. Preferred dopants include metal moieties of the alkaline and alkaline earth groups, especially lithium, magnesium or calcium moieties and also silicon, aluminium and gadolinium moieties. Usually the moiety is present as an oxide. The dopant may comprise from 0.1 to 40 wt% of a predominantly silicon carbide material.

The first component which, being able to withstand the operating temperature, is refractory is suitably in a physical form providing an extended surface for the catalytic reaction of the gas mixture. It may be particulate or pelleted or in the form of a structure such as a grid or honeycomb which presents a large surface area, and which may be formed by sintering.

The second component is provided on the surface of the first component and is an oxycompound of boron or phosphorus.

Typical oxycompounds of phosphorus are the alkali or alkaline earth metal salts of its oxyacids. Sodium, potassium, rubidium, caesium and barium salts have been found to be highly effective. Mixtures of two or more salts may be used. Mixed metal salts are of especial interest. The preferred oxyacid moieties are the orthophosphates and pyrophosphates although it should be explained that at the temperatures used in the performance of the method, both mono- and dihydrogen phosphates almost certainly decompose to form metaphosphates and/or polyphosphates (including pyrophosphates) and it is these decomposition products which will probably be the active moieties in practice. Accordingly it was surprising to discover that a catalyst system made using the monohydrogen orthophosphate was substantially more effective than one made using the dihydrogen orthophosphate and that a catalyst system made using the relatively thermally stable trimetal orthophosphate was in between the two in effectiveness.

Typical oxycompounds of boron are alkali metal borates (especially potassium metaborate) or boric acid which probably decomposes to boric oxide at the temperatures used in the performance of the method.

Preferably the oxycompound is provided or supported on the first component surface by impregnating the surface with a solution (preferably aqueous) of a boron or phosphorus compound. However for oxycompounds such as barium orthophosphate which are only sparingly soluble, it is possible to impregnate the surface with a solution of a soluble salt of the metal such as barium chloride and then perform an exchange reaction with a soluble orthophosphate solution such as aqueous sodium orthophosphate. When a particulate first component is impregnated and it is preferred that the particulate material should have a number average particle size of from 1 to 15 (especially 2 to 6) mm. After impregnation, the first component should be fired at a temperature of at least 700° C. (preferably 800° to 1000° C.). Firing should preferably be performed for a period of up to 6 hours (usually 3 to 5 hours) during which time decomposition of thermally decomposable oxycompounds may take place. The amount of oxycompound in the catalyst system is easily adjusted by varying the concentration of oxycompound (or its precursor) in the impregnating solution. Preferably the concentration of the impregnating solution should be adjusted to ensure that the fired catalyst system comprises from 0.1 to 40 (preferably 3 to 10) atomic % of cationic moiety (for example alkali or alkaline earth metal ion) and 0.05 to 20 atomic % of phosphorus or boron moiety.

Accordingly this invention also provides a catalyst system suitable for use in the oxidative conversion of methane to ethylene and/or ethane which system comprises one or more oxycompounds of boron or phosphorus provided on a surface of a non-reducible metal compound as described above which is sufficiently refractory to withstand a temperature of at least 500° C.

The method may be performed by passing the mixture of methane and oxygen through a tubular reaction zone at a flow rate chosen to give a contact time of from 0.1 to 10 (preferably 1.5 to 6) seconds between the mixture and the catalyst system. This is best achieved using a gas hourly space velocity of 100 to 200,000/hour.

The molar ratio of methane to oxygen in the mixture is preferably in the range of from 2:1 to 6:1. Higher ratios cause a significant decrease in the proportion of methane converted while lower ratios increase the amount of carbon dioxide formed. Similar results are obtained if the oxygen is diluted with inert gas, for example if air is used instead of oxygen provided of course similar ratios of methane to oxygen are maintained. The preferred operating pressure is atmospheric pressure although pressures of up to 100 bar may have some small benefit especially if the method is operated in the lower part of the temperature range, for example 500° to 800° C. Preferably any unconverted methane is mixed with a further quantity of oxygen to restore the required ratio of methane to oxygen and then re-cycled at least once through the reaction zone so as to contact the catalyst system.

This invention is illustrated by the following examples;

EXAMPLE 1

Preparation of catalyst systems

Particulate first component having a number mean particles size of 2.4 to 4 mm was impregnated with sufficient potassium monohydrogen orthophosphate $K_2HPO_4$ in an aqueous solution to produce a catalyst system containing 12 wt % of phosphorus moiety. Impregnation was performed by the incipient wetness technique which comprises soaking the first component in that volume of the aqueous solution of $K_2HPO_4$ which is just sufficient to fully saturate the first component and then drying the soaked first component at 150° C.

Finally the dried first component was fired at 850° C. for four hours.

EXAMPLE 2

Use of the catalyst systems

Methane was oxidatively converted to ethylene and ethane by passing a mixture of methane and oxygen through a quartz tube which was heated to various temperatures as specified in subsequent Examples and which contained in turn 30 g of the various catalyst systems again as specified in subsequent Examples. The molar ratio of methane to oxygen in the mixture was 3:1, the length and internal diameter of the tube were 200 mm and 4 mm respectively, the gas hourly space velocity through the catalyst system was 1300/hour, the contact time between mixture and catalyst system was about 3 seconds and the pressure within the tube was 3 bar.

EXAMPLE 3

This Example illustrates the use of pure zinc oxide as the first component of the catalyst system.

Pure zinc oxide was impregnated with $K_2HPO_4$ according to the procedure of Example 1 and used to convert methane to ethylene and ethane in accordance with the procedure of Example 2. The results obtained are shown in Table 1 from which it will be seen that the best selectivities to ethylene were obtained in the temperature range 800° C. to 900° C.

TABLE 1

| Temperature of the Catalyst System in the Quartz Tube °C. | Mol % of Methane Converted | Mol % Selectivity of the Conversion to the compounds specified below | |
|---|---|---|---|
| | | Ethylene | Ethane |
| 695 | 6 | 0 | 1 |
| 721 | 11 | 1 | 4 |
| 744 | 17 | 10 | 12 |
| 769 | 21 | 16 | 15 |
| 790 | 18 | 16 | 16 |
| 811 | 21 | 20 | 14 |
| 824 | 22 | 21 | 12 |
| 832 | 21 | 24 | 12 |
| 849 | 22 | 23 | 12 |
| 868 | 21 | 23 | 9 |
| 908 | 22 | 19 | 3 |
| 936 | 21 | 14 | 2 |
| 983 | 22 | 7 | 1 |

EXAMPLE 4

This Example illustrates how the percentage of methane converted can be increased by increasing the gas hourly space velocity.

The procedure of Example 3 was repeated except that the gas hourly space velocity (GHSV) was increased from 1300/hour to 120,000/hour as shown in Table 2.

TABLE 2

| Temp. of the Cat. System In Quartz tube °C. | Gas Hourly Space Velocity | Mol % of Methane Converted | Mol % Selectivity of the Conversion to the compounds specified below | |
|---|---|---|---|---|
| | | | Ethylene | Ethane |
| 849 | 1300/h | 22 | 23 | 12 |
| 847 | 12000/h | 22 | 33 | 10 |
| 891 | 60000/h | 28 | 22 | 2 |
| 904 | 120000/h | 30 | 22 | 2 |

EXAMPLE 5

This Example illustrates how the percentage of methane converted can be increased by using a first component containing dopants.

The procedure of Example 3 was repeated except that the zinc oxide was a commercial grade containing 3.1 wt % of calcium oxide and traces (less than 3 wt % in total) of iron, aluminium and titanium moieties and which is obtainable from Imperial Chemical Industries PLC under the code 32-4. The results obtained are shown in Table 3 which also shows corresponding results obtained with pure zinc oxide.

Table 3 shows that as compared with pure zinc oxide, the doped zinc oxide gave improved conversions of methane and about equally good selectivities to ethylene.

EXAMPLE 6

This Example illustrates the use of a silicon carbide containing dopant as the first component.

The procedure of Example 3 was repeated except that the first component used was Norton SZ 5245 which is a silicon carbide containing 28.5 wt % silica and 4.7 wt % alumina where the percentages are based on the total weight of the first component. The results obtained are shown in Table 4.

EXAMPLE 7

This Example illustrates the use of pure boron nitride. The procedure of Example 3 was repeated except that the first component used was pure boron nitride. The results obtained are shown in Table 4.

TABLE 3

| Temperature of the Catalyst System in the Quartz Tube °C. | Mol % of Methane Converted | Mol % Selectivity of the Conversion to the compounds specified below | |
|---|---|---|---|
| | | Ethylene | Ethane |
| Pure Zinc Oxide as first component | | | |
| 715 | 6 | 0 | 6 |
| 736 | 11 | 5 | 10 |
| 760 | 17 | 13 | 13 |
| 780 | 19 | 10 | 14 |
| 800 | 21 | 25 | 14 |
| 827 | 24 | 28 | 11 |
| 847 | 22 | 23 | 10 |
| 866 | 22 | 30 | 7 |
| 892 | 22 | 31 | 5 |
| 905 | 22 | 27 | 4 |
| 929 | 21 | 31 | 3 |
| Doped Zinc Oxide as first component | | | |
| 611 | 2 | 0 | 0 |
| 642 | 3 | 0 | 0 |
| 675 | 6 | 0 | 6 |
| 692 | 11 | 5 | 11 |
| 712 | 17 | 13 | 15 |
| 733 | 21 | 17 | 15 |
| 748 | 21 | 22 | 16 |
| 776 | 24 | 26 | 15 |
| 797 | 26 | 28 | 13 |

TABLE 3-continued

| Temperature of the Catalyst System in the Quartz Tube °C. | Mol % of Methane Converted | Mol % Selectivity of the Conversion to the compounds specified below | |
|---|---|---|---|
| | | Ethylene | Ethane |
| 823 | 26 | 32 | 11 |
| 844 | 27 | 33 | 9 |
| 863 | 27 | 30 | 7 |
| 893 | 27 | 28 | 4 |

TABLE 4

| First Component | Temp. of the Cat. System in the Quartz tube °C. | Mol % of Methane Converted | Mol % Selectivity of the Conversion to the compounds specified below | |
|---|---|---|---|---|
| | | | Ethylene | Ethane |
| Doped Silicon Carbide | 695 | 6 | 7 | 6 |
| | 722 | 7 | 9 | 7 |
| | 750 | 9 | 9 | 6 |
| | 780 | 10 | 13 | 8 |
| | 804 | 12 | 16 | 8 |
| | 819 | 13 | 16 | 8 |
| | 840 | 16 | 19 | 7 |
| | 857 | 24 | 18 | 4 |
| | 881 | 25 | 19 | 3 |
| | 903 | 26 | 19 | 2 |
| | 928 | 27 | 18 | 1 |
| | 955 | 29 | 16 | 1 |
| Pure Boron Nitride | 666 | 1 | 0 | 20 |
| | 715 | 6 | 5 | 13 |
| | 738 | 16 | 9 | 8 |
| | 760 | 22 | 18 | 6 |
| | 790 | 25 | 19 | 5 |
| | 800 | 26 | 17 | 4 |
| | 815 | 26 | 19 | 3 |
| | 844 | 27 | 19 | 2 |
| | 864 | 28 | 17 | 2 |
| | 888 | 28 | 17 | 1 |
| | 909 | 29 | 16 | 1 |

EXAMPLE 8

This example illustrates the use of calcium oxide as the first component of the catalyst system.

Pure calcium oxide was impregnated with $K_2HPO_4$ according to the procedure of Example 1. The catalyst system was used to convert methane to ethylene and ethane according to the procedure of Example 2 except that the gas hourly space velocity used was 12000/hour. The results obtained are shown in Table 5 from which it can be seen that the catalyst system achieved a good conversion efficiency and a good selectivity to ethylene at temperatures as low as 600° to 750° C.

TABLE 5

| Temp. of the Cat. System in the Quartz tube °C. | Mol % of Methane Converted | Mol % Selectivity of the Conversion to the compounds specified below | |
|---|---|---|---|
| | | Ethylene | Ethane |
| 587 | 3 | 21 | 15 |
| 621 | 21 | 26 | 16 |
| 635 | 22 | 25 | 15 |
| 654 | 22 | 25 | 14 |
| 708 | 17 | 19 | 9 |
| 715 | 23 | 22 | 10 |
| 717 | 21 | 24 | 11 |
| 743 | 13 | 23 | 10 |
| 774 | 23 | 20 | 7 |
| 797 | 23 | 20 | 6 |
| 824 | 24 | 19 | 4 |
| 861 | 24 | 18 | 3 |
| 904 | 23 | 19 | 1 |
| 937 | 25 | 15 | 1 |

EXAMPLE 9

This Example illustrates the use of gadolinium oxide as the first component of the catalyst system. The procedure of Example 3 was repeated except that the pure gadolinium oxide was impregnated with $K_2HPO_4$. The results of using this catalyst system to convert methane to ethylene and ethane in accordance with the procedure of Example 2 (except that the GHSV was 12000/hour) are shown in Table 6.

TABLE 6

| TEMP C | Mol % $CH_4$ conversion | Mol % selectivity of conversion to | |
|---|---|---|---|
| | | ethylene | ethane |
| 602 | 2 | 0 | 0 |
| 623 | 0 | 0 | 0 |
| 640 | 3 | 0 | 0 |
| 704 | 2 | 4 | 18 |
| 731 | 4 | 14 | 26 |
| 736 | 6 | 15 | 19 |
| 759 | 13 | 12 | 11 |
| 784 | 20 | 3 | 6 |
| 809 | 24 | 1 | 4 |
| 834 | 22 | 1 | 3 |
| 978 | 35 | 0 | 0 |

EXAMPLE 10

This Example illustrates the use of silica as the first component of the catalyst system. The procedure of Example 3 was repeated except that the $K_2HPO_4$ was impregnated into pure silica. The results of using this catalyst system to convert methane to ethylene and ethane in accordance with the procedure of Example 2 are shown in Table 7.

TABLE 7

| TEMP C | % $CH_4$ conversion | Mol % selectivity of conversion to | |
|---|---|---|---|
| | | ethylene | ethane |
| 680 | 8 | 1 | 4 |
| 707 | 13 | 5 | 8 |
| 733 | 20 | 10 | 9 |
| 752 | 24 | 16 | 9 |
| 778 | 28 | 23 | 8 |
| 804 | 29 | 24 | 7 |
| 812 | 27 | 28 | 9 |
| 830 | 26 | 29 | 7 |
| 847 | 27 | 27 | 5 |
| 863 | 27 | 23 | 3 |
| 880 | 28 | 25 | 2 |

EXAMPLE 11

This Example illustrates the use of a boron oxycompound as the second component of the catalyst system. Particulate $SiO_2$ was impregnated with sufficient boric acid ($H_3BO_3$) in aqueous solution to produce a catalyst system containing 10 wt % of boron moiety following the procedure of Example 1. The procedure of Example 2 was followed except that the gas hourly space velocity was 100/hour. The results are shown in Table 8.

TABLE 8

| TEMP C | % $CH_4$ conversion | Mol % selectivity of conversion to ethylene |
|---|---|---|
| 700 | 4.5 | negligible |
| 750 | 6.0 | 4.5 |
| 800 | 9.9 | 11.0 |

TABLE 8-continued

| TEMP C | % $CH_4$ conversion | Mol % selectivity of conversion to ethylene |
|---|---|---|
| 850 | 20.5 | 15.5 |

EXAMPLE 12

This Example further illustrates the use of the catalyst system as described in Example 10 but using a gas mixture of $CH_4:O_2:N_2=3:1:1$, at a GHSV of 12,000/hour. Table 9 shows the results.

TABLE 9

| TEMP C | Mol % $CH_4$ conversion | Mol % selectivity of conversion to | |
|---|---|---|---|
| | | ethylene | ethane |
| 697 | 2 | 0 | 5 |
| 718 | 2 | 0 | 13 |
| 744 | 3 | 6 | 22 |
| 754 | 4 | 10 | 25 |
| 791 | 12 | 21 | 17 |
| 823 | 23 | 27 | 19 |
| 848 | 27 | 32 | 7 |
| 867 | 27 | 32 | 7 |
| 893 | 26 | 29 | 4 |
| 917 | 25 | 28 | 3 |

EXAMPLE 13

This Example illustrates the use of zirconium oxide as the first component of the catalyst system. The procedure of Example 3 was repeated except that zirconium oxide was impregnated with $K_2HPO_4$. The results of using this catalyst system to convert methane to ethylene and ethane in accordance with the procedure of Example 2, except that the gas mixture was $CH_4:O_2:N_2=3:1:1$, are shown in Table 10.

TABLE 10

| TEMP C | % $CH_4$ conversion | Mol % selectivity of conversion to | |
|---|---|---|---|
| | | ethylene | ethane |
| 690 | 9 | 0 | 1 |
| 711 | 15 | 3 | 5 |
| 733 | 16 | 8 | 9 |
| 757 | 20 | 11 | 10 |
| 781 | 23 | 15 | 10 |
| 803 | 23 | 15 | 10 |
| 835 | 23 | 15 | 8 |
| 850 | 21 | 17 | 8 |
| 870 | 20 | 17 | 6 |

The following illustrates the effect of the second component on an $SiO_2$ first component. The figures are % ethylene selectivity at various temperatures, other reaction conditions being the same.

| 2nd component | 750° C. | 800° C. | 850° C. | 900° C. |
|---|---|---|---|---|
| none | 2.2 | 3.5 | 9 | 11 |
| 10% $K_3PO_4$ | 2.4 | 8.5 | 19 | |
| 10% $H_3BO_3$ | 3.6 | 3.9 | 17 | |
| 5% $B_2O_3$ - 5% $P_2O_5$ | 3.6 | 5.3 | 12 | |
| 10% $KBO_2$ | 5.5 | 4.5 | 9 | 14 |

COMPARATIVE EXAMPLE A

This Example illustrates the use of a multivalent cation in the first component.

The procedure of Example 3 was repeated except that the first component was chromium oxide ($Cr_2O_3$). The results are shown in Table 11.

TABLE 11

| Temperature of the Catalyst System in the Quartz Tube °C. | Mol % of Methane Converted | Mol % Selectivity of the Conversion to the compounds specified below | |
|---|---|---|---|
| | | Ethylene | Ethane |
| 628 | 10 | 1 | 3 |
| 705 | 15 | 1 | 3 |
| 735 | 15 | 2 | 3 |
| 762 | 16 | 1 | 2 |
| 783 | 16 | 1 | 2 |
| 796 | 16 | 1 | 2 |
| 825 | 16 | 1 | 2 |
| 850 | 17 | 1 | 1 |
| 877 | 16 | 2 | 2 |
| 898 | 17 | 3 | 2 |
| 922 | 19 | 4 | 2 |
| 944 | 20 | 5 | 1 |
| 967 | 21 | 6 | 1 |

COMPARATIVE EXAMPLE B

This Example further illustrates the use of a multivalent cation in the first component.

The procedure of Example 3 was repeated except that the first component was titanium dioxide ($TiO_2$) and the gas mixture was $CH_4:O_2:N_2=3:1:1$, used at a GHSV of 12000/hour.

The results are shown in Table 12.

TABLE 12

| TEMP C | % $CH_4$ conversion | Mol % selective conversion to | |
|---|---|---|---|
| | | ethylene | ethane |
| 713 | 6 | 5 | 11 |
| 754 | 9 | 3 | 4 |
| 772 | 3 | 0 | 0 |
| 793 | 19 | 15 | 7 |
| 815 | 21 | 7 | 5 |
| 846 | 19 | 7 | 3 |
| 943 | 33 | 5 | 0 |

What is claimed is:

1. A catalyst system suitable for use in the oxidative conversion of methane to ethylene which comprises a first support component which is a non-reducible metal compound and which first component is substantially refractory at a temperature of 500°–1000° C. and a second component which is one or more oxycompounds selected from the group consisting of boron and phosphorus supported on the surface of the first component.

2. A catalyst system as claimed in claim 1 in which the non-reducible metal compound is selected from the group consisting of BeO, MgO, CaO, SrO, BaO, $Sc_2O_3$, $Y_2O_3$, $La_2O_3$, $ZrO_2$, $HfO_2$, $Ta_2O_5$, ZnO, $GeO_2$, $SiO_2$, SiC, BN, $Nd_2O_3$, $Gd_2O_3$, $Dy_2O_3$, $Ho_2O_3$, $Er_2O_3$ and $Lu_2O_3$.

3. A catalyst system as claimed in claim 1 in which the first component is selected from the group consisting of and CaO.

4. A catalyst system as claimed in claim 1 in which the first component is $SiO_2$.

5. A catalyst system as claimed in claim 1 in which the first component is selected from the group consisting of BN, SiC and ZnO and contains from 0.1 to 40 wt % of a dopant.

* * * * *